United States Patent [19] | [11] Patent Number: 4,800,163
Hibi et al. | [45] Date of Patent: Jan. 24, 1989

[54] FLOW CHAMBER AND ELECTRO-MANIPULATOR INCORPORATING SAME

[75] Inventors: Tadaaki Hibi; Miyoji Sugiura; Hiromi Kano, all of Tsukuba; Sigeyuki Kimura, Hino; Takeshi Kazami, Tsukuba, all of Japan

[73] Assignees: Ntl. Inst. of Agrobiological Resources, Ibargi; Nihon Bunko Kogyo Kabushiki Kaisya, Tokyo, both of Japan

[21] Appl. No.: 133,722

[22] Filed: Dec. 15, 1987

[30] Foreign Application Priority Data

Dec. 15, 1986 [JP] Japan .................. 61-297925
Dec. 15, 1986 [JP] Japan .................. 61-297926

[51] Int. Cl.⁴ .................. C12M 1/00; C12N 13/00
[52] U.S. Cl. .................. 435/287; 435/173; 417/118; 417/567; 417/568; 204/299 R; 204/180.1; 935/93; 935/94; 935/89
[58] Field of Search .................. 435/287, 173; 935/93, 935/94, 89; 204/299 R, 180.1; 417/118, 137, 567, 568

[56] References Cited

U.S. PATENT DOCUMENTS

| 3,078,868 | 2/1963 | Lamb | 417/118 X |
|---|---|---|---|
| 3,175,688 | 3/1965 | Zink | 435/316 X |
| 3,460,810 | 8/1969 | Moeller | 435/316 X |
| 4,441,972 | 4/1984 | Pohl | 204/183.1 |
| 4,578,167 | 3/1986 | Schoner | 204/299 R X |
| 4,695,547 | 9/1987 | Hilliard et al. | 435/287 X |

FOREIGN PATENT DOCUMENTS

| 696481 | 8/1940 | Fed. Rep. of Germany | 417/137 |
|---|---|---|---|
| 0054713 | 3/1985 | Japan | 204/299 R |
| 1209592 | 9/1986 | Japan | 435/287 |
| 428752 | 10/1974 | U.S.S.R. | 435/287 |

OTHER PUBLICATIONS

Physiol Plant 67: 507–516, Copenhagen 1986, Zachrisson et al., Electromanipulation of Plant Protoplast.
J.gen Virol (1986), 67: 2037–2042, Hibi et al., High Efficiency Electro-Transfection of Tobacco Mesophyll Proplasts with Tobacco Mosaic Virus RNA.
Angew.Chem. Int. Ed Engl. 20. 325–344, 1981, Zimmermann et al., Cells with Manipulated Funtions: New Perspectives for Cell Biology, Medicine, and Technology.

*Primary Examiner*—Samuel Scott
*Assistant Examiner*—Carl D. Price
*Attorney, Agent, or Firm*—Browdy & Neimark

[57] ABSTRACT

A sample stored in a reservoir is introduced into a flow chamber having a pair of panel electrodes interposed by an insulating flat plate spacer having an opening. After electro-fusion is completed or while electro-transfection is being conducted by the application of a suitable voltage between the panel electrodes, fused cells or cells that have been transfected with nucleic acids are discharged out of the flow chamber, and the sample in the reservoir is simultaneously introduced into the flow chamber. This cycle of operations is repeated.

8 Claims, 7 Drawing Sheets

[ELECTRO-FUSION PATTERN]

FIG. 7

FLOW CHAMBER AND ELECTRO-MANIPULATOR INCORPORATING SAME

BACKGROUND OF THE INVENTION

1. Field of the Invention

The present invention relates to a flow chamber and an electro-manipulator incorporating the same which enables continuous flow electro-fusion or electro-transfection.

2. Description of the Prior Art

Electro-fusion which was developed and established by Zimmermann et al in 1981 relies on the following principle. A cell suspension is introduced into a space between the electrodes disposed in parallel. When an alternating current is applied between the electrodes, the cells are moved in an electric field in the direction of the highest field strength and are oriented into a configuration resembling of a pearl chain. Application of direct-current pulses having a duration ranging between several $\mu s$ to several tens of $\mu s$ to the cells in this state induces reversible disorder of the lipid bilayers constituting the cell membranes and reassembly thereof, which leads to fusion of the cells (Angew. Chem. Int. Ed Engl. 20. 325-344, 1981; PHYSIOL. PLANT. 67:50 7-516. Copenhagan 1986).

Electro-transfection is a technique developed in 1982 by Neumann et al. This involves the introduction of a mixture of cells and nucleic acids between the electrodes and application of direct-current pulses having a duration ranging between several $\mu s$ to several tens of $\mu s$ between the electrodes which causes introduction (transfection) of the nucleic acids into the cells.

The present inventors have developed a chamber which includes a flat-sided spacer having a notch and a pair of gold evaporated glass panel electrodes separated by the spacer, and the use of this chamber has made it possible for them to increase the cell fusion rate and nucleic acid transfection rate up to 96% and 95%, respectively (J. Gen. Virol., 1986, 67, 2037-2042).

Known chambers, however, require manual replacement of samples used for electro-fusion or electro-transfection. With such chamber, therefore, it has been impossible to process a large number of cells in a short period of time. In addition, the known chambers require a complicated series of operations.

SUMMARY OF THE INVENTION

Accordingly, an object of the present invention is to provide a flow chamber and an electro-manipulator incorporating the same which can be operated easily, and which are capable of continuously conducting electro-fusion or electro-transfection on a large amount of cells.

To achieve this object, the present invention provides in one of its aspects a flow chamber for use in electro-maninuplation which comprises: a spacer made of an electrically insulating flat plate, the spacer having an opening formed therein so as to form a chamber; a pair of electrode members interposed by the spacer, the opposing surfaces of the electrode members being made flat; an inlet communicating with the chamber formed by the spacer and the pair of electrode members; and an outlet communicating with the chamber formed by the spacer and the pair of electrode members.

The present invention provides in another of its aspects an electro-manipulator which comprises: a reservoir for storing a sample on which electro-fusion or electro-transfection is to be conducted; the flow chamber provided in the first aspect of the present invention whose inlet is connected to the outlet of the reservoir; sample transferring means for introducing the sample into the chamber of the flow chamber and discharging the electro-manipulated sample from the outlet of the flow chamber; and means for applying a voltage between the pair of electrodes of the flow chamber so as to conduct electro-fusion or electro-transfection.

DESCRIPTION OF THE PREFERRED EMBODIMENTS

Figure 1:
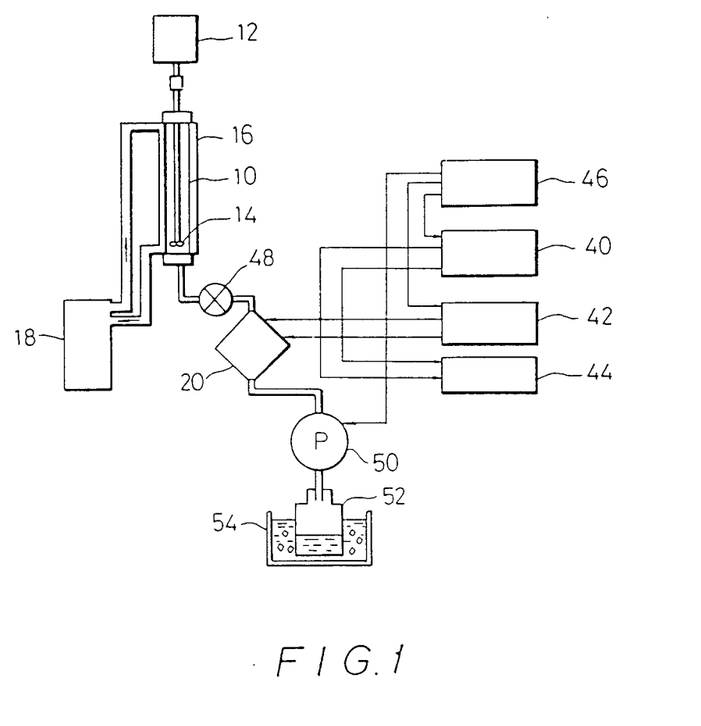
FIG. 1 is a schematic view is an electro-manipulator, showing a first embodiment of the present invention.

A first embodiment of the present invention will be described below with reference to FIGS. 1 to 4. FIG. 1 schematically illustrates the structure of an electro-manipulator.

In the electro-manipulator of FIG. 1, reference numeral 10 denotes a reservoir 10 for storing a large amount of a sample on which electro-fusion or electro-transfection is to be conducted.

Numeral 12 denotes a stirrer having a propeller 14 that is inserted within the reservoir 10 so as to cause the sample stored in the reservoir 10 to be homogenized by the low-speed rotation thereof.

Numeral 16 denotes a water jacket which is provided in such a manner as to enclose the reservoir 10 and through which constant-temperature water is passed.

Numeral 18 denotes a constant-temperature water tank with a pump. An inlet pipe and an outlet pipe of the tank 18 are respectively connected to an outlet pipe and an inlet pipe of the water jacket 16 which are provided at the lower and upper ends thereof so as to provide a circulation of the constant-temperature water in the direction indicated by the arrows.

Numeral 20 denotes a flow chamber where electro-manipulation is conducted on cells introduced therein.

Figure 2A:
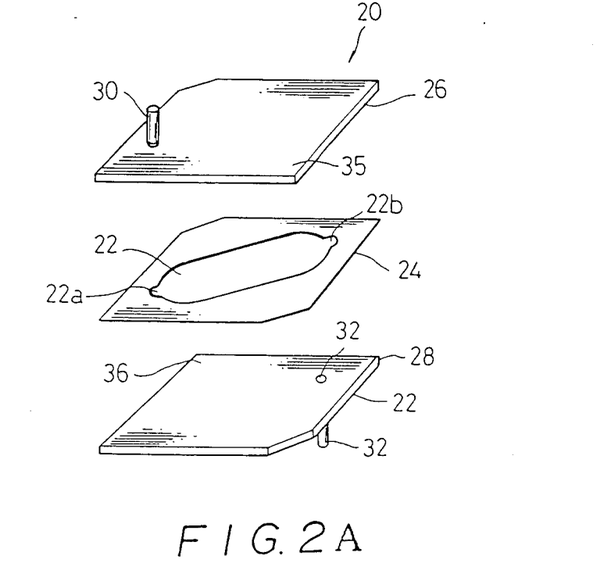
FIG. 2A is an exploded perspective view of a flow chamber 20 incorporated in the electro-manipulator of FIG. 1, showing the concrete structure thereof.
Figure 2B:
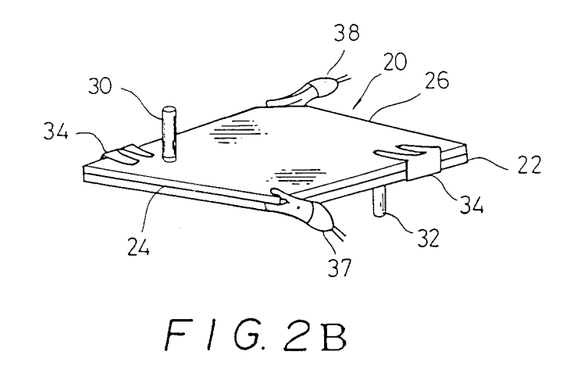
FIG. 2B is a perspective view of the flow chamber 20 of FIG. 2A, showing it in an assembled state.

An example of the flow chamber structure 20 will be shown in FIGS. 2A and 2B in which FIG. 2A is an exploded perspective view of the flow chamber and FIG. 2B is a perpspective view thereof showing it in an assembled state.

The flow chamber 20 includes a a flat spacer 24 which has an opening 22 formed at the central portion thereof, and panel electrodes 26 and 28 separated by the spacer 24. The spacer 24 is made of an electrically insulating plate, e.g., a polyvinyl chloride plate, having a thickness of 200 μm. The longitudinal ends of the opening 22 are shaped with a streamlined form so that no sample will remain there. Substantially semi-circular notches 22a and 22b are formed at the two longitudinal ends of the opening 22. The panel electrodes 26 and 28 are made of, for example, mirror polished glass plates with opposing surfaces on which gold is coated. Each of the panel electrodes 26 and 28 is provided with a hole which corresponds to the notch 22a or 22b, and into which one end of an inlet pipe 30 or an outlet pipe 32 is fitted. The inlet and outlet pipes 30 and 32 are mounted at the opposing corners of the opening 22. The panel electrodes 26 and 28 are placed one on top of the other with the spacer 24 interposed therebetween, and are gripped by clips 34. One corner of each of the panel electrodes 26 and 28 is cut off, and a terminal portion 35 or 36 formed at the corner opposite the cut corner is gripped by an alligator clip 37 or 38 which serves as an electrode connecting terminal.

As shown in FIG. 1, the alligator clips 37 and 38 are parallel-connected to the output terminal of an oscillator 40, the output terminal of a pulse generator 42, and the input terminal of an oscilloscope 44. A controller 46 controls the turning on/off of the output of the oscillator 40 and the switching of the amplitude of its output, as well as the turning on/off of the output of the pulse generator 42.

Reference numeral 48 denotes a stop valve inserted in a piping which connects the outlet of the reservoir 10 to the inlet of the flow chamber 20 to open and close its flow passage.

Numeral 50 denotes a suction pump whose inlet is connected to the outlet of the flow chamber 20. Under the control of the controller 46, the suction pump 50 is adapted to introduce the sample stored in the reservoir 10 into the flow chamber 20 and discharge it out of the flow chamber 20 after electro-manipulation is completed, or while it is being conducted.

Numeral 52 denotes a tank which is connected to the outlet of the suction pump 50 for storing the electro-manipulated sample.

Numeral 54 denotes a cooling tank for cooling the tank 52.

It is noted that the oscillator 40 is employed only for electro-fusion and that no oscillator is necessary to perform electro-transfection. Although the temperature to be attained for electro-fusion differs in accordance with the type of cell or the activity thereof, it usually ranges between 4° and 25° C. On the other hand, in the case of electro-transfection, the temperature must in general be 0° C. in order to delay the speed at which the cell membranes are repaired and thereby increase the nucleic acid transfection rate.

Conventionally, electro-manipulation has been conducted in a sterilized room so as to prevent the contamination of the sample. In the case of the electro-manipulator of this embodiment, however, the reservoir 10, the flow chamber 20, the suction pump 50, the tank 52 and the cooling tank 54 may be accommodated in a box supplied with sterilized air, and the need for sterilizing the entirety of the room in which the electro-manipulator is installed may be eliminated.

The operation of the thus-arranged electro-manipulator will now be described. The first part of the description is related to the operation of the electro-manipulator which is used for electro-fusion.

While observing the waveform of the output of the oscillator 40 and pulse generator 42 by means of the oscilloscope 44, the frequency and amplitude of the output of the oscillator 40, the duration and voltage of the output pulses of the pulse generator 42, and the number of pulses generated by the pulse generator 42 during one operation are manually and suitably set in accordance with the thickness of the spacer 24, the type of sample and the flow rate set. If the cells employed are plant protoplasts, these factors are set at the following values: the frequency and the strength of the electric field generated between the electrodes by the oscillator 40 are set at values ranging between 0.5 and 2 MHz and between 100 and 500 $V_{p-p}$/cm, respectively. The duration, strength of the electric field and intervals between the pulses generated from the pulse generator 42 range between 10 μs and 1 ms, between 0.5 and 2 kV/cm, and between 10 ms and 1 s, respectively.

A cell suspension is fed to the reservoir 10 as a sample.

The stirrer 12 is operated to stir the sample so that the density of the cells is made uniform.

Subsequently, the stop valve 48 is opened, and the controller 46 is activated so as to automatically perform the following processes in sequence.

First, the controller 46 turns on the suction pump 50 for a predetermined period of time so as to introduce the sample stored in the reservoir 10 into the flow chamber 20 until the flow chamber is filled with the sample.

Figure 3:
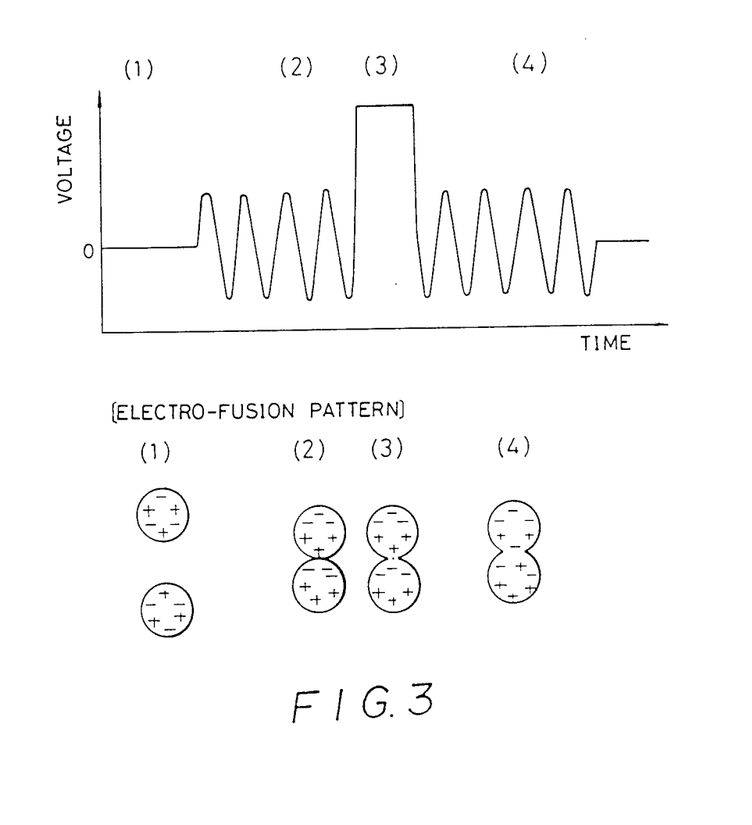
FIG. 3 illustrates the sequence of stages of electro-fusion.

Next, the controller 46 controls the oscillator 40 and the pulse generator 42 and thereby applies a voltage sequence such as that shown in FIG. 3 between the electrodes of the flow chamber 20.

The sequence of stages of electro-fusion caused by the application of the voltage sequence is shown schematically in FIG. 3. Stage (1) represents the state in which no voltage is being applied. In stage (2), the cells are oriented in the direction of an electric field in a pearl-chain fashion, caused by the application of an alternating current from the oscillator 40. In stage (3), localized collapse of cell membranes occurs at the point of contact between adjacent cells, caused by the application of direct-current pulses from the pulse generator 42. Finally, in stage (4), the assembly of the cell membranes and fusion of the cells occur, caused by the application of the alternating voltage alone from the oscillator 40.

Thereafter, the controller 46 stops applying the voltage, then turns on the suction pump 50 for a predetermined period of time so as to discharge the electro-manipulated sample in the flow chamber 10 into the tank 52 and cause the non-manipulated sample stored in the reservoir 10 to flow into the flow chamber 20. Repetition of the above-described cycle of processes enables electro-fusion to be continuously conducted on a large amount of sample in a short period of time, thus making mass-production of useful hybrid fused cells possible.

Figure 4:
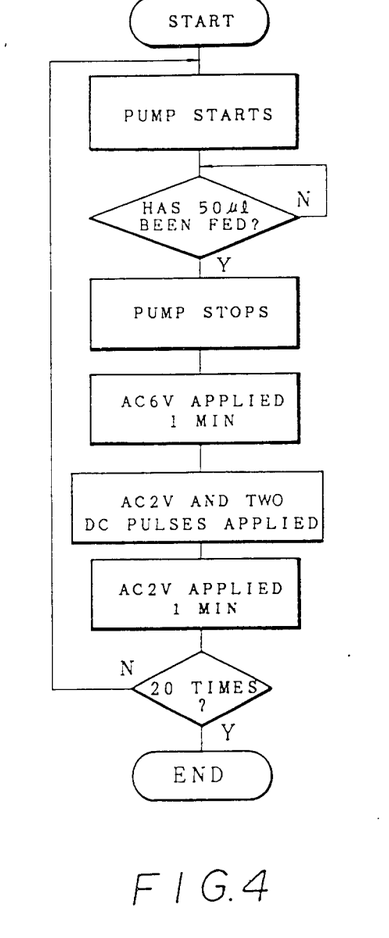
FIG. 4 is a flowchart of the processing of electro-fusion, showing an example thereof.

A test example of electro-fusion will be described below with reference to the flowchart shown in FIG. 4. A flow chamber 20 having a volume of 50 μand an inter-electrode distance of 200 μm was used. Tobacco mesophyll protoplasts (cv: Xanthi NN) suspended at a concentration of about $2 \times 10^5$ cells/m l in 0.5 M-mannitol containing 100 μM $CaCl_2$ were employed as the sample. The controller 46 was equipped with a setting device for setting the number of times the sample was charged into and discharged from the flow chamber 20, and the setting device was set to 20.

The suction pump 50 was turned on for a predetermined time in a state wherein the stirrer 12 was being driven, so as to feed 50 μof sample into the flow chamber 20. An AC voltage of 6 V and 500 kHz in frequency was applied between the electrodes for one minute to cause the cells to be aligned in a pearl-chain configuration. Subsequently, two rectangular DC pulses having a voltage of 40 V and a duration of 50 μs were appolied (at an interval of 1 second) while an AC voltage of 2V, reduced from the 6 V, was being applied in order to induce temporary collapse of the cell membranes. Thereafter, an AC voltage of 2V and 500 kHz was applied for one minute to induce electro-fusion. The suction pump 50 was then turned on for a predetermined time, so that the fused cells in the flow chamber 20 were discharged into the tank 52 and another 50 μof non-manipulated sample stored in the reservoir 10 was fed into the flow chamber 20. This cycle of operations was repeated 20 times (the number of times set), which enabled a total of 1 ml, or approximately $2 \times 10^5$ cells, to be manipulated. A total of 40 minutes (equal to 2 minutes per cycle$\times$20 times) was required to complete the test. The cell fusion rate attained was about 42%, and approximately 70% of the fused cells was binuclear.

A second test example of electro-fusion which has recently been conducted will be described below. A flow chamber 20 having a volume of 5 ml and an inter-electrode distance of 2 mm was employed. The same sample as that employed in the first test example was used.

The suction pump 50 was turned on for a predetermined time in a state wherein the stirrer 12 was being driven, so as to feed 5 ml of sample into the flow chamber 20. An AC voltage of 20 V and 500 kHz in frequency was applied between the electrodes for about one minute to cause the cells to be aligned in a pearl-chain configuration. Subsequently, two rectangular DC pulses having a voltage of 160 V and a duration of 50 μs were applied (at an interval of 1 second) while an AC voltage of 20 V was being applied in order to induce temporary collapse of the cell membranes. The application of 20 VAC was terminated concurrently with the turning off of the second DC pulse. Unlike in the first test example, cell fusion was induced without the application of an alternating voltage after the turning off of the DC pulses. Subsequenlty, the suction pump 50 was turned on for a predetermined time, so that the fused cells in the flow chamber 20 was discharged into the tank 52 and another 5 ml of non-manipulated sample stored in the reservoir 10 was fed into the flow chamber 20. This cycle of operations was repeated 20 times (the number of times set), which enabled a total of 100 ml, or approximately $2 \times 10^7$, cells to be manipulated. A total of 20 minutes (equal to 1 minute per cycle$\times$20 times) was required to complete the test. The cell fustion rate attained was about 42%, and approximately 70% of the fused cells was binuclear.

In other words, the second test produced 100 times as many fused cells than the first test, in half the time.

When the above-described flow chamber having a volume of 5 ml was used to conduct electro-fusion of tobacco mesophyll protoplasts with carrot root protoplasts, the generation rate of the binucleate heterokarions was about 10% of the entire protoplasts. The speed at which the binucleate heterokarions were formed was about $1 \times 10^5$/min.

Next, the operation of the electro-manipulator will be described with regard to electro-transfection.

In electro-transfection, the constant-temperature tank with a pump 18 is activated to cool the sample in the reservoir 10. The suction pump 50 is turned on, and DC pulses are applied periodically between the electrodes of the flow chamber 20 by the pulse generator 42 while the suction pump 50 is kept on. If the cells used are plant protoplasts, the frequency of the DC pulses is set to a value which ensures that the sample receives about 10 pulses while it is located within the flow chamber 20. The duration and height of the pulses are set to values which range between 10 μs and 1 ms and which ensures that the strength of the electric field generated by the application of pulses ranges between 0.5 and 2 kV/cm, respectively.

Application of DC pulses induces localized collapse and reassembly of cell membranes, during which the nucleic acids attached to the collapsed membranes are introduced into the cells.

A test example of this transfection of nucleic acids will now be described. The same electro-manipulator as that described above was used, with the exception of the flow chamber. The flow chamber used had a volume of 50 μl and an inter-electrode distance of 0.5 mm. Tobacco mesophyll protoplasts (cv: Xanthi NN) which were suspended at a concentration of approximately $2 \times 10^5$ cells/ml in 0.5 M-mannitol with 100 μM $MgCl_2$ and which were mixed with tobacco mosaic virus (TMV) RNA at a concentration of 10 μg/ml, were employed as the sample. Pulses having a height of 40 V and a duration of 50 μs were applied at a frequency of 10 cycles/s to this sample while it was being continuously fed by the suction pump 50 at a rate of 50 μl/s. This operation was continued for 80 seconds, until a total of 4 ml or $8 \times 10^5$ of protoplasts were obtained. The transfection rate of the nucleic acids and survival rate of the cells were 96% and 95%, respectively.

In the embodiment described above, a feed pump which substitutes for the suction pump 50 may be provided in the flow passage between the reservoir 10 and the flow chamber 20.

If a flow chamber having a larger volume is employed, the processing speed may be increased. However, there is a limitation to this increase, determined by the performance of the oscillator and pulse generator, and the use of a flow chamber of a very large volume is not economical.

Figure 5:
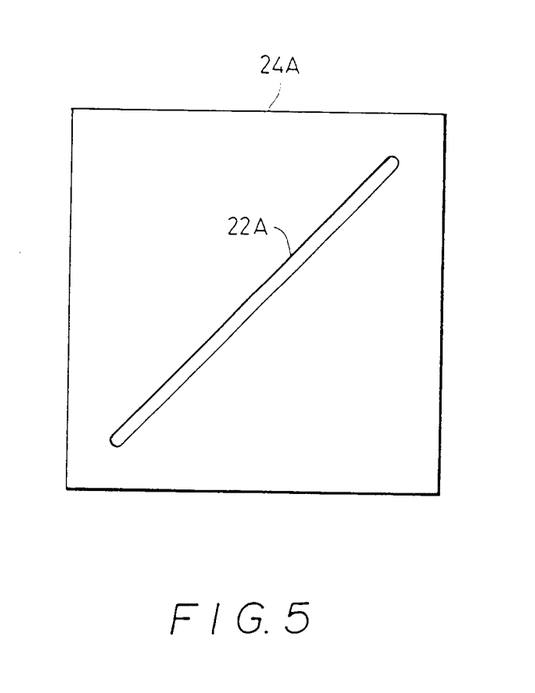
FIG. 5 is a plan view of spacer which is a constituent of the flow chamber and which is used for electro-transfection, showing another example thereof.

Another example of a spacer will be described below with reference to FIG. 5.

A spacer 24A has an elongated opening 22A formed along one diagonal thereof. This type of spacer can be used for electro-transfection. The opening 22A has a width which is equal to the inner diameter of the inlet pipe 30 and outlet pipe 32 shown in FIG. 2A, and which is, for example, 2 mm. The length of the opening 22A is, for example, 40 mm. The inlet pipe 30 and the outlet pipe 32 are mounted on the corresponding panel electrodes in such a manner that they are located at the opposing two ends of the opening 22A.

Use of this spacer 24A ensures that no sample remains in the electrodes, and therefore increases a nucleic acid transfection rate and a cell survival rate from those obtained with the spacer 24 of FIG. 2A.

Next, another example of the structure of flow chamber and its auxiliary devices will be described with reference to FIG. 6.

In this flow chamber, an outlet pipe 32A is mounted on the panel electrode 28 at a position at which it faces the inlet pipe 30 mounted on the panel electrode 26. An operation pipe 58A which corresponds to the outlet pipe 32 shown in FIG. 2A is located above the inlet pipe 30. A check valve 60 and a check valve 62 are connected to the inlet pipe 30 and the outlet pipe 32A, respectively. A reversible pump 50A is connected to the operation pipe 58A.

The thus-arranged flow chamber is operated in the manner described below.

The air in the flow chamber is sucked out by the reversible pump 50A, so that the check valve 60 is opened and the check valve 62 is closed, and the sample in the reservoir is introduced into the flow chamber through the check valve 60 and the inlet pipe 30. The reversible pump 50A is stopped in a state wherein the flow chamber is filled with the sample, and electro-fusion is then performed by applying a voltage sequence between the panel electrodes 26 and 28 in the manner described above.

Subsequently, the air is charged into the flow chamber by the reversible pump 50A, so that the check valve 60 is closed and the check valve 62 is opened, and the sample in the flow chamber is discharged into the tank through the outlet pipe 32A and the check valve 62.

This cycle of processes is repeated to continuously conduct the electro-fusion.

When an electro-manipulator incorporating this flow chamber was used to conduct electro-fusion on the sample prepared in the manner described above, a maximum of cell fusion rate of 96% was achieved.

If electro-transfection is conducted using a electro-manipulator with this flow chamber, the sample in the flow chamber is continuously sucked out by the reversible pump 50A.

A still another example of the structure of the flow chamber and its auxiliary devices will be described below with reference to FIG. 7.

Figure 6:
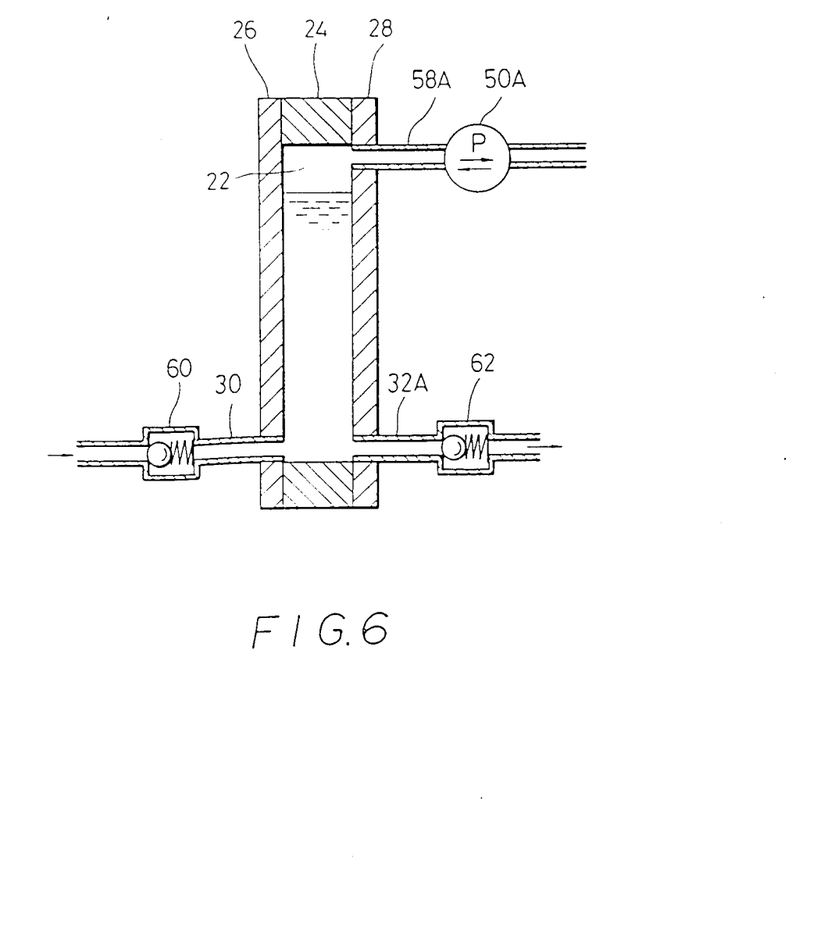
FIG. 6 is a schematic view of a flow chamber and its periphery, showing another example thereof.

In this example, no pipe which corresponds to the outlet pipe 32A of FIG. 6 is mounted on the panel electrode 28, and one end of a T-shaped pipe 30A is mounted on the electrode 26 at a position at which the inlet pipe 30 of FIG. 6 is mounted. The remaining two ends of the T-shaped pipe 30A are connected to the check valves 60 and 62, respectively. Other arrangement and the operation are identical with those of the example shown in FIG. 6.

Various other modifications of the present invention are possible without departing from the scope of the invention as set forth in the appended claims.

In addition to that used in the above-described embodiments, the panel electrodes may be made of any material which ensures that the irregularities on the panel surface are made sufficiently small when compared with the size of the cell, which does not impart mechanical damage to the cell membranes, and which does not readily cause electrolysis. Suitable materials of the substrates of the panel electrodes include mirror polished quartz, sapphire, plastic, aluminum and stainless steel. Suitable metals that can be coated on the substrates include platinum and titanium. The metal flat plates such as platinum, titanium or stainless steel that are electrolytic polished may also be used to make panel electrodes.

Provision of the inlet pip 30 and the outlet pipe 32 may be replaced by the formation of an inlet groove and an outlet groove in the spacer, these grooves being provided by constructing a spacer as two half parts and by locating these two parts with a small gap provided therebetween.

A cylinder within which a piston is moved back and forth may be employed in place of the reversible pump 50A shown in FIG. 6.

Figure 7:
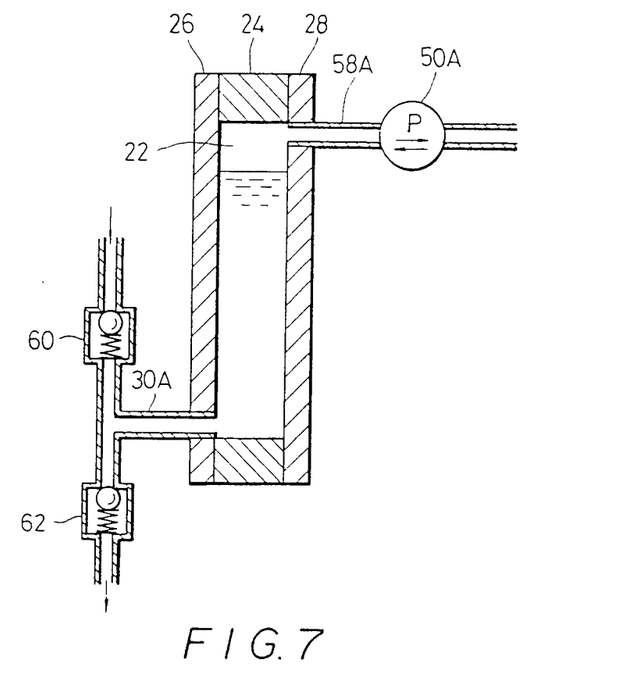
FIG. 7 is a schematic view of the flow chamber and its periphery, showing still another example thereof.

The check valves 60 and 62 shown in FIGS. 6 and 7 may be replaced by solenoid valves which open and close the flow passages. The check valves 60 and 62 shown in FIG. 6 may also be replaced by a 3-port solenoid change-over valve provided at the intersection of the T-shaped pipe 30A.

In the examples shown in FIGS. 6 and 7, there is in general no necessity for detecting the amount of sample in the flow chamber. However, it may be detected by, for example, detecting the electrostatic capacity between the panel electrodes 26 and 28, if desired.

What is claimed is:

1. An electro-manipulator comprising:
   a reservoir for storing a sample on which electrofusion or electro-transfection is to be conducted, said reservoir having an outlet from which said sample is discharged;
   a flow chamber including a spacer made of an electrically insulating flat plate, said spacer having two flat opposing surfaces, said spacer having an opening formed between and through said flat opposing surfaces so as to in part form a chamber, a first flat electrode member placed on one of said flat opposing surfaces and a second flat electrode member placed on the other of said flat opposing surfaces with said spacer therebetween, an inlet, an outlet, and an operation port, said inlet, said outlet and said operation port communicating with said chamber formed by said spacer and said first and second electrode members;
   a sample introducing passageway for connecting said outlet of said reservoir to said inlet of said flow chamber;
   a downstream flow passage connected to said outlet of said flow chamber;
   sample transferring means connected to said operation port of said flow chamber for decreasing the pressure in said flow chamber when said sample is to be introduced into said flow chamber and for increasing the pressure in said flow chamber when said sample is to be discharged from said flow chamber;
   flow passage switch-over means for opening said sample introducing passageway while closing said downstream flow passage at said outlet of said flow chamber when the pressure in said flow chamber is decreased by said sample transferring means, and for closing said sample introducing means while opening said downstream flow passage when the pressure in said flow chamber is increased by said sample transferring means; and
   means for carrying out electro-fusion or electrotransfection by the application of a voltage between said first and second electrode members of said flow chamber.

2. An electro-manipulator according to claim 1, wherein said electrode members are made of a mirror polished flat plate with a thin film of gold, platinum, or titanium coated thereon.

3. An electro-manipulator according to claim 2, wherein said inlet of said flow chamber is provided in said first electrode member while said outlet of said flow chamber is provided in said second electrode member.

4. An electro-manipulator according to claim 2, wherein said sample transferring means comprises a reversible pump.

5. An electro-manipulator according to claim 2, wherein said reservoir has a stirrer for stirring said sample such that said sample becomes homogenized.

6. An electro-manipulator according to claim 2, wherein said reservoir has constant temperature means for maintaining a desired temperature of said sample at a set value.

7. An electro-manipulator according to claim 2, wherein said inlet and said outlet of said flow chamber comprise a single inlet/outlet port.

8. An electro-manipulator according to claim 2, wherein said flow passage switch-over means comprises a check valve.

* * * * *